United States Patent
Sontyana et al.

(10) Patent No.: US 11,779,914 B2
(45) Date of Patent: Oct. 10, 2023

(54) HYDROALKYLATION OF MONONUCLEAR AROMATIC HYDROCARBONS TO MONO CYCLOALKYL AROMATIC HYDROCARBONS

(71) Applicants: Bharat Petroleum Corporation Limited, Uttar Pradesh (IN); Indian Institute of Technology Delhi, New Delhi (IN)

(72) Inventors: Ananth Kishore Kumar Sontyana, Uttar Pradesh (IN); Nikita Sharma, Uttar Pradesh (IN); Shivanand Mukund Pai, Uttar Pradesh (IN); Bharat Lakshman Newalkar, Uttar Pradesh (IN); Kamal Kishore Pant, New Delhi (IN)

(73) Assignees: BHARAT PETROLEUM CORPORATION LIMITED, Uttar Pradesh (IN); INDIAN INSTITUTE OF TECHNOLOGY DELHI, New Delhi (IN)

(*) Notice: Subject to any disclaimer, the term of this patent is extended or adjusted under 35 U.S.C. 154(b) by 67 days.

(21) Appl. No.: 17/477,768

(22) Filed: Sep. 17, 2021

(65) Prior Publication Data
US 2022/0088582 A1    Mar. 24, 2022

(30) Foreign Application Priority Data
Sep. 18, 2020 (IN) .............................. 202011040546

(51) Int. Cl.
*B01J 37/02* (2006.01)
*B01J 37/08* (2006.01)
(Continued)

(52) U.S. Cl.
CPC ......... *B01J 37/0213* (2013.01); *B01J 8/0242* (2013.01); *B01J 21/04* (2013.01);
(Continued)

(58) Field of Classification Search
CPC ...... B01J 37/0213; B01J 8/0242; B01J 21/04; B01J 23/755; B01J 29/146; B01J 37/0009;
(Continued)

(56) References Cited

U.S. PATENT DOCUMENTS 6,303,530 B1 * 10/2001 Schwartz ............. B01J 37/0009
502/262
6,413,898 B1 * 7/2002 Faber ....................... B01J 35/04
502/64
(Continued)

*Primary Examiner* — Ali Z Fadhel
(74) *Attorney, Agent, or Firm* — D'Ambrosio & Menon, PLLC; Usha Menon

(57) ABSTRACT

An aspect of the present disclosure relates to a process for preparing a composite hydroalkylation catalyst including: (a) effecting impregnation of a hydrogenation metal on an inorganic oxide to form a metal impregnated inorganic oxide; (b) effecting calcination of the metal impregnated inorganic oxide to obtain a calcined metal impregnated inorganic oxide; (c) preparing a composite mixture comprising a molecular sieve, the calcined metal impregnated inorganic oxide and a binder; (d) preparing an extruded catalyst; and (e) effecting calcination of the extruded catalyst to obtain the composite hydroalkylation catalyst. The composite hydroalkylation catalyst prepared using this process affords dramatic improvement in conversion of mononuclear aromatic hydrocarbon and the yield of the hydroalkyled mononuclear aromatic hydrocarbon (e.g. CHB).

14 Claims, 2 Drawing Sheets

(51) Int. Cl.
*B01J 37/04* (2006.01)
*B01J 37/00* (2006.01)
*B01J 21/04* (2006.01)
*B01J 23/755* (2006.01)
*B01J 37/16* (2006.01)
*B01J 8/02* (2006.01)
*C07C 2/84* (2006.01)
*C07C 7/04* (2006.01)
*C07C 5/367* (2006.01)
*B01J 29/14* (2006.01)

(52) U.S. Cl.
CPC .......... *B01J 23/755* (2013.01); *B01J 29/146* (2013.01); *B01J 37/0009* (2013.01); *B01J 37/04* (2013.01); *B01J 37/082* (2013.01); *B01J 37/16* (2013.01); *C07C 2/84* (2013.01); *C07C 5/367* (2013.01); *C07C 7/04* (2013.01); *B01J 2229/20* (2013.01); *C07C 2521/04* (2013.01); *C07C 2523/755* (2013.01)

(58) Field of Classification Search
CPC . B01J 37/04; B01J 37/082; B01J 37/16; B01J 2229/20; B01J 8/0492; B01J 8/0453; C07C 2/84; C07C 5/367; C07C 7/04; C07C 2521/04; C07C 2523/755; C07C 2529/14; C07C 2601/14; C07C 2/74
See application file for complete search history.

(56) References Cited

U.S. PATENT DOCUMENTS

| | | | |
|---|---|---|---|
| 10,226,766 B2* | 3/2019 | Kijlstra | B01J 29/084 |
| 2010/0249479 A1* | 9/2010 | Berg-Slot | B01J 37/0009 |
| | | | 502/66 |
| 2012/0129959 A1* | 5/2012 | Jothimurugesan | B01J 35/108 |
| | | | 502/328 |
| 2013/0165730 A1* | 6/2013 | Bouchy | C10G 45/64 |
| | | | 585/739 |
| 2014/0046109 A1* | 2/2014 | Ghosh | C07C 2/864 |
| | | | 502/77 |
| 2019/0321809 A1* | 10/2019 | Ghosh | B01J 29/123 |
| 2021/0178372 A1* | 6/2021 | Lee | B01J 37/04 |

* cited by examiner

HYDROALKYLATION OF MONONUCLEAR AROMATIC HYDROCARBONS TO MONO CYCLOALKYL AROMATIC HYDROCARBONS

CROSS REFERENCE TO RELATED APPLICATION(S)

This application is related to and claims priority to Indian Patent Application No. 202011040546 filed on Sep. 18, 2020, the contents of which are incorporated by reference herein.

FIELD OF THE INVENTION

The present invention is related to the catalyst and a process of producing cyclohexylbenzene by contacting benzene and hydrogen in a distributed feed reactor loaded with hydroalkylation catalyst.

BACKGROUND

Cyclohexylbenzene (hereinafter also referred to as "CHB") is an important product in the chemical industry, and it has the following applications:

a) CHB is a valuable solvent and important intermediate for fine chemicals.
b) It is used for the preparation of phenol and cyclohexanone by hydroperoxidation and the co-produced cyclohexanone is a useful intermediate for the manufacture of adipic acid, caprolactam and nylon.
c) It offers an alternative route for producing biphenyl (Heat transfer fluid) by dehydrogenation.
d) It is used as Heat transfer fluid and as an electrolyte additive for overcharge protection of lithium ion battery.
e) It is also used as intermediate for liquid crystal display (LCD) material.
f) It is also utilized as a penetrating agent in the textile industry.
g) It is also used in pharmaceuticals and dyeing industry.
h) Bicyclohexyl can be produced by the hydrogenation of CHB and the produced bicyclohexyl can be used as liquid organic hydrogen carrier (LOHC) in the transportation industry.

It is well known that, when benzene is heated with hydrogen in presence of hydroalkylation catalyst, benzene undergoes partial hydrogenation to form cyclohexene which then alkylates with benzene to produce CHB. Hydroalkylation reaction can be carried out in variety of reactors like batch, semi batch, slurry, reactive distillation columns, upflow/down flow fixed bed reactor. Typical reaction temperature for the hydroalkylation reaction is about 80 to 270 C and typical reaction pressure for the hydroalkylation of benzene is about 1 bar to 100 bar. Typical values of the weight hourly space velocities for the hydroalkylation reaction are about 0.05 to 50 $hr^{-1}$. Typical values for the hydrogen to benzene mole ratios for the hydroalkylation reaction are about 0.1 to 10. Below Figure illustrates the reaction schema for the hydroalkylation of benzene.

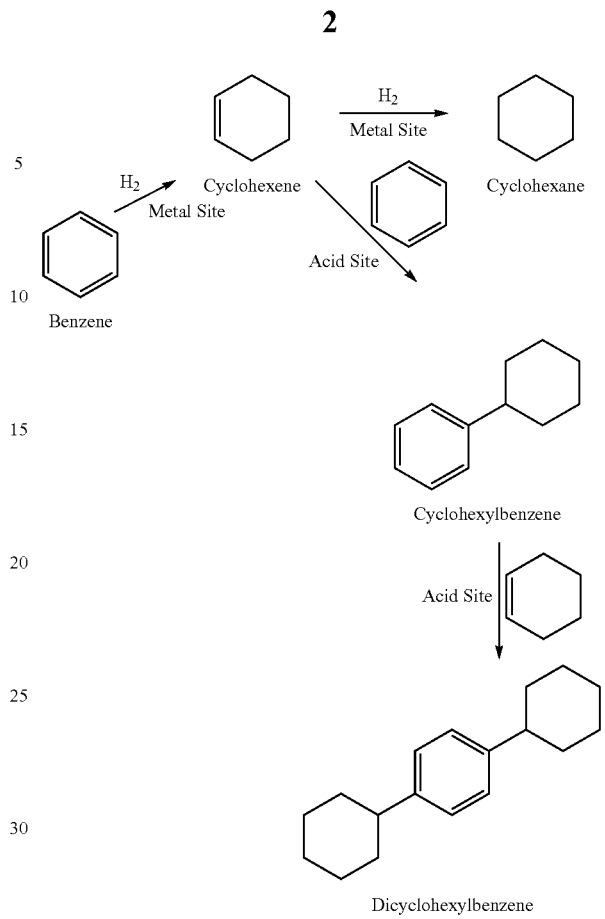

Benzene is hydrogenated to cyclohexene along with little amount of cyclohexane over the metal sites of the catalyst. Cyclohexene reacts with benzene on the acid sites of the catalyst to form the main product CHB. Byproduct like dicyclohexylbenzene (DCHB) can also form due to the alkylation of cyclohexene with CHB on the acid sites of the catalyst. From the above reaction pathways, it would be clear that the hydroalkylation catalyst is a dual function catalyst consisting of metal sites for hydrogenation and acid sites for the alkylation.

Currently the most common process for producing CHB is by direct alkylation of benzene with cyclohexene using sulfuric acid as catalyst. Benzene reacts with cyclohexene to form mono, di, tri and tetracyclohexylbenzenes. The nature of the products depends on the amount of cyclohexene in the reaction mixture. Mono, di, tri and tetra CHB react with cyclohexene to form higher derivatives. Mono, di, tri and tetra cyclohexylbenzenes react with benzene to form lower derivatives. Main drawbacks of this process are—usage of hazardous chemicals (such as sulfuric acid) in the process, and low selectivity for CHB due to large quantities of higher derivatives produced due to the reaction of CHB with cyclohexene.

CHB can also be produced by hydrogenation of biphenyl using noble metal catalysts. However, due to high cost of noble metal catalyst and biphenyl, this method is not implemented for industrial production. It is also well known in literature that when benzene is heated with hydrogen in presence of hydroalkylation catalyst, benzene undergoes partial hydrogenation to form cyclohexene which then alkylates with benzene to produce CHB.

Yamazaki et al. (Y. Yamazaki, A. Masuda, T. Kawai, S. Kimura, *Bulletin of Japan Petroleum Institute*, 18 (1976) 25-31) carried out the hydroalkylation of benzene on series of nickel supported silica-alumina catalyst and studied the effect of catalyst pretreatment and reaction conditions on the catalyst activity in batch reactor. This study reported that selectivity of CHB is proportional to the number of acid sites and silica-alumina with 42wt. % of alumina was the best support for the hydroalkylation reaction due to higher acidity of the support. Author also studied the effects of catalyst metal content on the hydroalkylation activity and selectivity. Activity of the catalyst increased with nickel content of the catalyst; however, CHB selectivity decreased due to higher hydrogenation activity with increased metal loading. Furthermore, activity of the catalyst increased with increase in reduction temperature without affecting product selectivities. Nickel content of 3-5 wt. %, catalyst reduction temperature of 723-773K, catalyst calcination temperature of 973-1073 K and reaction temperature of 473 K were found to be optimal. The best catalyst, 5 wt. % Ni loaded on silica-alumina exhibited a selectivity of 64% for CHB at 35% benzene conversion.

U.S. Pat. No. 3,412,165 describes a method of preparation CHB by contacting benzene with hydrogen in the presence of a catalyst comprising of tungsten, hydrogenation metal supported on halogen activated silica alumina support. The reaction of this invention can be carried out at a temperature of 100-400° C., Hydrogen pressure of 400-1500 psi and LHSV of 0.1-4. Reaction products from the reactor are passed to several distillation columns to separate benzene, cyclohexane, CHB and trimers as individual components and the separated benzene is recycled back to the reactor. The inventor claimed that, by conducting the hydroalkylation reaction in a down flow reactor will lead to excessive hydrogenation leading to lower CHB selectivity. In case of upflow reactor, wherein benzene and hydrogen are fed to the bottom of the reactor showed higher CHB selectivity and better catalyst stability. CHB selectivity of 64.5% was achieved at a benzene conversion of 29% using a catalyst containing 1.4 wt % platinum, 8.4wt % tungsten and 2.04 wt % of fluorine.

U.S. Pat. No. 4,268,699 describes a method of hydroalkylation of benzene in presence of a catalyst comprising of ruthenium and nickel supported on zeolite of type X or type Y. The reaction of this invention was carried out at a temperature of 180-230° C. and LHSV of 10-30. CHB selectivity of 73% was achieved at a benzene conversion of 16.7% using a catalyst containing 0.1wt % ruthenium and 0.1 wt % nickel.

U.S. Pat. No. 5,053,571 describes a method of preparation CHB by contacting benzene with hydrogen in the presence of a catalyst prepared using incipient wetness method, the catalyst comprising 1-3 wt % ruthenium and 0.5-1 wt % nickel supported on zeolite beta. The hydroalkylation reaction can be carried out at a liquid hourly space velocity (LHSV) ranging from 1 to 100, a reaction pressure ranging from 100 to 1000 kPa, a hydrogen feed rate ranging from 0.2 to 6 mole per mole of feedstock per hour, and a reaction temperature ranging from 100 to 300° C. CHB selectivity of 37.2% was achieved at a benzene conversion of 45.7% using a catalyst containing 1 wt % ruthenium, 0.5 wt % tungsten and 0.5 wt % of nickel.

U.S. Pat. No. 5,146,024 describes a method for the production of CHB, wherein benzene reacts with hydrogen in the presence of carbon monoxide (process modifier) and Nickel, Lanthanum and Palladium supported X or Y zeolite to form CHB. The hydroalkylation reaction can be carried out at a liquid hourly space velocity (LHSV) ranging from 1 to 100, a reaction pressure ranging from 50 to 1500 psig, molar ratio of hydrogen to benzene 0.2:1 to about 1:1, molar ratio of CO to hydrogen 0.02:1 to about 0.1:1 and a reaction temperature ranging from 100 to 250° C. CHB selectivity of 71.14% was achieved at a benzene conversion of 47.2% using a catalyst containing 0.5 wt % palladium, 2-25wt % lanthanum and 0.01-12 wt % nickel.

U.S. Pat. No. 6,037,513 discloses that CHB can be produced by contacting benzene with hydrogen in the presence of a bifunctional catalyst consisting of a molecular sieve MCM-22 and at least one hydrogenation metal selected from palladium, ruthenium, nickel and cobalt. Hydroalkylation reaction can be carried out at a weight hourly space velocity (WHSV) ranging from 0.01 to 100, a reaction pressure ranging from 100 to 7000 kPa, molar ratio of benzene to hydrogen 0.01 to 100, and a reaction temperature ranging from 50 to 350° C. The catalyst for this process was prepared using wetness impregnation with aqueous solution of various metals salts on MCM-22 extrudates consisting of 65 wt % MCM-22 and 35 wt % $Al_2O_3$ binder. After 22 days of on stream, CHB selectivity of 71.4% was achieved at a benzene conversion of 43.9% using a catalyst containing 0.3 wt % ruthenium and 0.3 wt % tin.

Although numerous approaches have been reported so far, the conventional benzene hydroalkylation catalysts suffer from the problem of low selectivity to CHB, leading to economic/industrial non-viability of benzene conversion. Large quantities of unwanted products like cyclohexane, methylcyclopentane, methylcyclopentyl-cyclohexylbenzene and dicyclohexylbenzene also form along with CHB due to complex reaction chemistry. Furthermore, most of the conventional catalysts contain higher percent of noble metal for the hydrogenation function making the catalyst expensive. All the above factors are hindering the commercial application of benzene hydroalkylation process.

U.S. Pat. No. 3,784,617 discloses a process for the hydroalkylation of benzene, wherein benzene and hydrogen are partially hydroalkylated in first stage reactor and this partially hydroalkylated stream is cooled and reacted with second portion of hydrogen in the second stage of hydroalkylation reactor thus producing the final product. Using this process hydroalkylation reaction temperature can be better controlled and the hydroalkylation product will have less undesirable impurities. After two such passes, CHB selectivity of 67% was achieved at a benzene conversion of 46.6% using a catalyst containing 19 wt % tungsten and 6 wt % nickel supported on mixture of silica-alumina and HY zeolite.

U.S. Pat. No. 8084648 discloses a process for the hydroalkylation of benzene using a recycle reactor, wherein benzene and hydrogen are introduced into the reaction zone under hydroalkylation conditions to produce CHB. The reaction effluent stream consisting of CHB and benzene is divided into two portions. The first portion of the effluent stream is cooled and recycled back to the reaction zone and the second portion of the effluent stream go to the second section of the reaction zone. After 2 stages of operation, CHB selectivity of 81.3% was achieved at a benzene conversion of 31.0%. According to this report, cooling and recycling part of the reaction effluent from the reaction zone, allows improved temperature control such that the hydroalkylation reaction can be operated near isothermal condition and the selectivity for the CHB can be maximized. This report describes a hydroalkylation process with better selectivity for CHB by employing a scheme having better reaction temperature control leading to a reactor effluent stream with minimum impurities.

However, the above processes suffer from the problem of low benzene conversion and low selectivity to CHB.

In view of the above, there is a long felt need to develop an economical and environmentally benign catalyst for effecting hydroalkylation. Need is also felt of an efficient process for converting benzene to CHB that affords higher yield of CHB with reduced formation of the impurities. Need is also felt of integration of a hydroalkylation reactor with a catalytic reforming unit of an oil refinery that precludes the need for separating close boiling benzene and cyclohexane.

OBJECTS

An object of the present disclosure is to provide an improved composite hydroalkylation catalyst.

Another object of the present disclosure is to provide an improved method for preparation of a composite hydroalkylation catalyst.

Another object of the present invention is to provide an efficient process for converting benzene to CHB using a distributed feed reactor.

Yet another object of the present invention is to integrate hydroalkylation process with Continuous Catalytic Reforming (CCR) unit of a refinery.

SUMMARY

An aspect of the present disclosure relates to a process for preparing a composite hydroalkylation catalyst, said process including the steps of: (a) effecting impregnation of a hydrogenation metal on an inorganic oxide to form a metal impregnated inorganic oxide; (b) effecting calcination of the metal impregnated inorganic oxide at a temperature ranging from 250° C. to 500° C. for a time period ranging from 1 hour to 15 hours to obtain a calcined metal impregnated inorganic oxide; (c) preparing a composite mixture comprising a molecular sieve, the calcined metal impregnated inorganic oxide and a binder; (d) kneading the composite mixture to obtain an extruded catalyst; and (e) effecting calcination of the extruded catalyst at a temperature ranging from 250° C. to 400° C. to obtain the composite hydroalkylation catalyst.

In an embodiment, the process further includes a step of subjecting the composite hydroalkylation catalyst to reduction. In an embodiment, the composite hydroalkylation catalyst is subjected to reduction at a temperature ranging from 200° C. to 500° C. for a time period ranging from 3 hours to 20 hours.

In an embodiment, the composite mixture comprises the molecular sieve, the calcined metal impregnated inorganic oxide and the binder in a weight ratio ranging from 1:1:1 to 50:30:1. In an embodiment, the step of calcination of the metal impregnated inorganic oxide is effected at a temperature ranging from 250° C. to 500° C. in air for a time period ranging from 3 hours to 10 hours. In an embodiment, the step of calcination of the extruded catalyst is effected at a temperature ranging from about 250° C. to about 400° C. under constant air flow for a time period ranging from 1 hour to 5 hours.

In an embodiment, the molecular sieve is selected from zeolite Y, zeolite X, zeolite Beta, Mordenite, MCM-22 and mixtures thereof. In an embodiment, the hydrogenation metal is selected from Palladium, Ruthenium, Nickel, Cobalt, Platinum, Rhodium, Rhenium, Tin, Zinc and mixtures thereof. In an embodiment, the inorganic oxide comprises alumina, silica, silica-alumina, titania, zirconia and mixtures thereof. In an embodiment, the binder is selected from clays, silica, alumina, silica-alumina, metal oxides and mixtures thereof.

In an embodiment, the molecular sieve is zeolite Y, said zeolite Y being USY zeolite, the hydrogenation metal is nickel, the inorganic oxide comprises alumina and the binder is alumina. In an embodiment, the molecular sieve has $SiO_2/Al_2O_3$ ratio ranging between 4 and 200. In an embodiment, amount of the metal impregnated on the inorganic oxide ranges from 5 wt % to 50 wt %. In an embodiment, the amount of the metal impregnated in the composite hydroalkylation catalyst ranges from 0.1 wt. % to 30 wt. %.

Another aspect of the present disclosure relates to a process for hydroalkylation of a mononuclear aromatic hydrocarbon in a distributed feed reactor having a plurality of reactor zones, said process comprising the steps of:

(i) feeding a stream comprising the mononuclear aromatic hydrocarbon and hydrogen at one or more positions along length of the distributed feed reactor; and (ii) effecting passage of the mononuclear aromatic hydrocarbon and hydrogen concurrently through a catalyst bed to effect hydroalkylation of the mononuclear aromatic hydrocarbon, said catalyst bed comprising a composite hydroalkylation catalyst, wherein said composite hydroalkylation catalyst is prepared by a process comprising the steps of: (a) effecting impregnation of a hydrogenation metal on an inorganic oxide to form a metal impregnated inorganic oxide; (b) effecting calcination of the metal impregnated inorganic oxide at a temperature ranging from 250° C. to 500° C. for a time period ranging from 1 hour to 15 hours to obtain a calcined metal impregnated inorganic oxide; (c) preparing a composite mixture comprising a molecular sieve, the calcined metal impregnated inorganic oxide and a binder; (d) preparing an extruded catalyst from the composite mixture; and (e) effecting calcination of the extruded catalyst at a temperature ranging from 250° C. to 400° C. to obtain the composite hydroalkylation catalyst.

In an embodiment, the composite hydroalkylation catalyst is subjected to reduction at a temperature ranging from 200° C. to 500° C. for a time period ranging from 3 hours to 20 hours before being packed in the catalyst bed.

In an embodiment, the mononuclear aromatic hydrocarbon is benzene, and the reactor zones are operated at a pressure ranging from 5-60 bar and at a temperature ranging from 100° C. to 300° C. In an embodiment, molar ratio of hydrogen to benzene fed to the reactor ranges from 0.5:1 to 5:1.

In an embodiment, the molecular sieve is selected from zeolite Y, zeolite X, zeolite Beta, Mordenite, MCM-22 and mixtures thereof. In an embodiment, the hydrogenation metal is selected from Palladium, Ruthenium, Nickel, Cobalt, Platinum, Rhodium, Rhenium, Tin, Zinc and mixtures thereof. In an embodiment, the inorganic oxide comprises alumina, silica, silica-alumina, titania, zirconia and mixtures thereof. In an embodiment, the binder is selected from clays, silica, alumina, silica-alumina, metal oxides and mixtures thereof. In an embodiment, amount of the metal impregnated in the composite hydroalkylation catalyst ranges from 0.1 wt. % to 30 wt. %. In an embodiment, the molecular sieve is zeolite Y, said zeolite Y being USY zeolite, the hydrogenation metal is nickel, the inorganic oxide comprises alumina and the binder is alumina. In an embodiment, the molecular sieve has $SiO_2/Al_2O_3$ ratio ranging between 4 and 200.

Still further aspect of the present disclosure relates to a process for operating a hydroalkylation reactor integrated with a catalytic reforming unit of an oil refinery, the process including the steps of: (i) subjecting a reactor effluent stream comprising unconverted hydrogen, benzene, cyclohexane, cyclohexylbenzene (CHB) and dicyclohexylbenzene (DCHB) from the hydroalkylation reactor to a separator to obtain unconverted hydrogen and a separated stream comprising the remainder of the components; (ii) subjecting the separated stream to fractional distillation to obtain a $C_6$ rich stream comprising cyclohexane and unconverted benzene and one or more streams comprising cyclohexylbenzene and dicyclohexylbenzene; (iii) blending the $C_6$ rich stream with naphtha feed to obtain a feed stream; (iv) feeding the feed stream to the catalytic reforming unit affording conversion of cyclohexane present in the feed stream to benzene; and (v) feeding benzene and hydrogen obtained from the catalytic reforming unit to the hydroalkylation reactor.

BRIEF DISCRIPTION OF THE DRAWINGS

DETAILED DESCRIPTION

Figure 1:
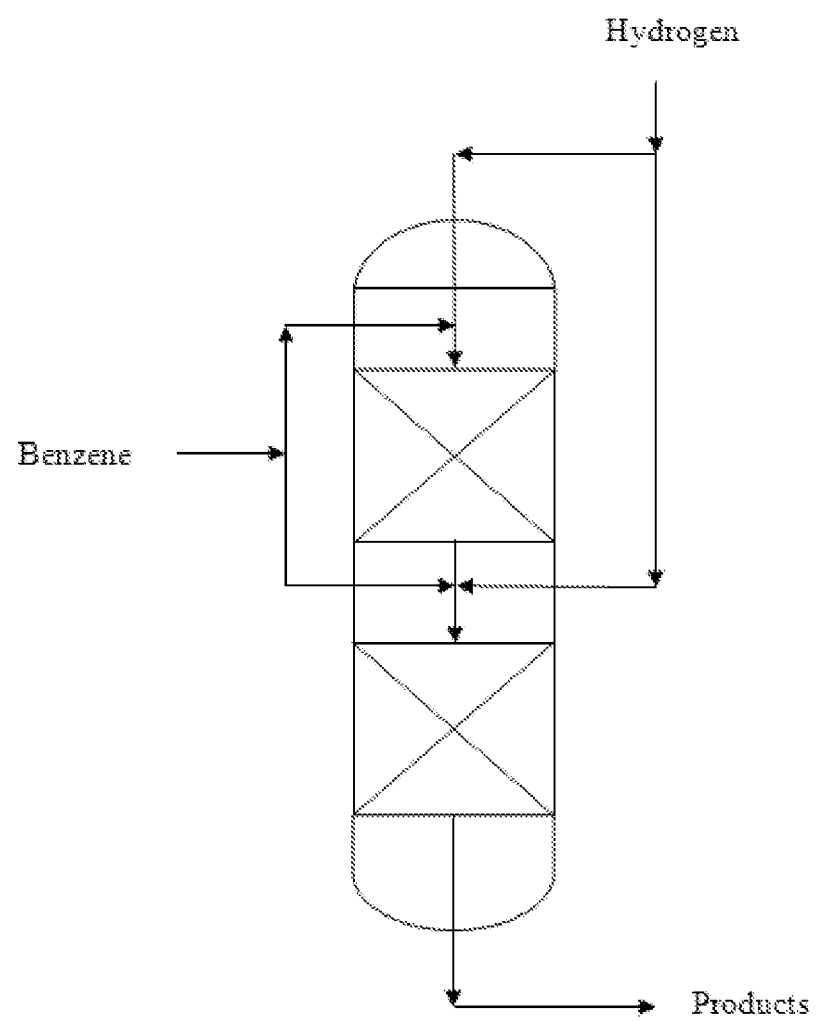
FIG. 1 illustrates an exemplary schematic diagram of a distributed feed hydroalkylation reactor, wherein benzene and hydrogen feeds are distributed uniformly along the length of the reactor.

The present disclosure is, in part, on the premise of a surprising observation of the inventors that the composite hydroalkylation catalyst prepared using a process that includes two (2) calcination steps viz. (i) effecting calcination of the metal impregnated inorganic oxide; and (ii) effecting calcination of the extruded catalyst affords dramatic improvement in conversion of mononuclear aromatic hydrocarbon and the yield of the hydroalkyled mononuclear aromatic hydrocarbon (e.g. CHB).

Accordingly, an aspect of the present disclosure relates to a process for preparing a composite hydroalkylation catalyst, said process including the steps of: (a) effecting impregnation of a hydrogenation metal on an inorganic oxide to form a metal impregnated inorganic oxide; (b) effecting calcination of the metal impregnated inorganic oxide at a temperature ranging from 250° C. to 500° C. for a time period ranging from 1 hour to 15 hours to obtain a calcined metal impregnated inorganic oxide; (c) preparing a composite mixture comprising a molecular sieve, the calcined metal impregnated inorganic oxide and a binder; (d) kneading the composite mixture to obtain an extruded catalyst; and (e) effecting calcination of the extruded catalyst at a temperature ranging from 250° C. to 400° C. to obtain the composite hydroalkylation catalyst.

In an embodiment, the process further includes a step of subjecting the composite hydroalkylation catalyst to reduction. In an embodiment, the composite hydroalkylation catalyst is subjected to reduction at a temperature ranging from 200° C. to 500° C. for a time period ranging from 3 hours to 20 hours.

In an embodiment, the composite mixture comprises the molecular sieve, the calcined metal impregnated inorganic oxide and the binder in a weight ratio ranging from 1:1:1 to 50:30:1. In an embodiment, the composite mixture comprises the molecular sieve, the calcined metal impregnated inorganic oxide and the binder in a weight ratio ranging from 1:1:1 to 25:10:1. In an embodiment, the composite mixture comprises the molecular sieve, the calcined metal impregnated inorganic oxide and the binder in a weight ratio ranging from 1:1:1 to 15:5:1. In an embodiment, the composite mixture comprises the molecular sieve, the calcined metal impregnated inorganic oxide and the binder in a weight ratio ranging from 1:1:1 to 5:2:1. In an embodiment, the composite mixture comprises the molecular sieve, the calcined metal impregnated inorganic oxide and the binder in a weight ratio ranging from 3:1.2:1 to 5:2:1. In an embodiment, the composite mixture has relative proportions of molecular sieve to calcined metal impregnated inorganic oxide to binder varying between 0.1 to 0.88 wt. % of molecular sieve, 0.4 to 0.1 wt. % calcined metal impregnated inorganic oxide, 0.5 to 0.02 wt. % binder.

In an embodiment, the molecular sieve is selected from zeolite Y, zeolite X, zeolite Beta, Mordenite, MCM-22 and mixtures thereof. In an embodiment, the hydrogenation metal is selected from Palladium, Ruthenium, Nickel, Cobalt, Platinum, Rhodium, Rhenium, Tin, Zinc and mixtures thereof. In an embodiment, the inorganic oxide comprises alumina, silica, silica-alumina, titania, zirconia and mixtures thereof. In an embodiment, the binder is selected from clays, silica, alumina, silica-alumina, metal oxides and mixtures thereof.

In an embodiment, the molecular sieve is zeolite Y, said zeolite Y being USY zeolite, the hydrogenation metal is nickel, the inorganic oxide comprises alumina and the binder is alumina. In an embodiment, the molecular sieve has $SiO_2/Al_2O_3$ ratio ranging between 4 and 200. In an embodiment, amount of the metal impregnated on the inorganic oxide ranges from 5 wt % to 50 wt %. In an embodiment, the amount of the metal impregnated in the composite hydroalkylation catalyst ranges from 0.1 wt. % to 30 wt. %.

In an embodiment, the step of calcination of the metal impregnated inorganic oxide is effected at a temperature ranging from 250° C. to 500° C. in air for a time period ranging from 3 hours to 10 hours. In an embodiment, the step of calcination of the extruded catalyst is effected at a temperature ranging from about 250° C. to about 400° C. under constant air flow for a time period ranging from 1 hour to 5 hours.

Another aspect of the present disclosure relates to a process for hydroalkylation of a mononuclear aromatic hydrocarbon in a distributed feed reactor having a plurality of reactor zones, said process comprising the steps of:

(i) feeding a stream comprising the mononuclear aromatic hydrocarbon and hydrogen at one or more positions along length of the distributed feed reactor; and (ii) effecting passage of the mononuclear aromatic hydrocarbon and hydrogen concurrently through a catalyst bed to effect hydroalkylation of the mononuclear aromatic hydrocarbon, said catalyst bed comprising a composite hydroalkylation catalyst, wherein said composite hydroalkylation catalyst is prepared by a process comprising the steps of: (a) effecting impregnation of a hydrogenation metal on an inorganic oxide to form a metal impregnated inorganic oxide; (b) effecting calcination of the metal impregnated inorganic oxide at a temperature ranging from 250° C. to 500° C. for a time period ranging from 1 hour to 15 hours to obtain a calcined metal impregnated inorganic oxide; (c) preparing a composite mixture comprising a molecular seive, the calcined metal impregnated inorganic oxide and a binder; (d) preparing an extruded catalyst from the composite mixture; and (e) effecting calcination of the extruded catalyst at a temperature ranging from 250° C. to 400° C. to obtain the composite hydroalkylation catalyst.

In an embodiment, the composite hydroalkylation catalyst is subjected to reduction at a temperature ranging from 200° C. to 500° C. for a time period ranging from 3 hours to 20 hours before being packed in the catalyst bed.

In an embodiment, the mononuclear aromatic hydrocarbon is benzene, and the reactor zones are operated at a pressure ranging from 5-60 bar and at a temperature ranging from 100° C. to 300° C. In an embodiment, molar ratio of hydrogen to benzene fed to the reactor ranges from 0.5:1 to 5:1.

In an embodiment, the molecular sieve is selected from zeolite Y, zeolite X, zeolite Beta, Mordenite, MCM-22 and mixtures thereof. In an embodiment, the hydrogenation metal is selected from Palladium, Ruthenium, Nickel, Cobalt, Platinum, Rhodium, Rhenium, Tin, Zinc and mixtures thereof. In an embodiment, the inorganic oxide comprises alumina, silica, silica-alumina, titania, zirconia and mixtures thereof. In an embodiment, the binder is selected from clays, silica, alumina, silica-alumina, metal oxides and mixtures thereof. In an embodiment, amount of the metal impregnated in the composite hydroalkylation catalyst ranges from 0.1 wt. % to 30 wt. %. In an embodiment, the molecular sieve is zeolite Y, said zeolite Y being USY zeolite, the hydrogenation metal is nickel, the inorganic oxide comprises alumina and the binder is alumina. In an embodiment, the molecular sieve has $SiO_2/Al_2O_3$ ratio ranging between 4 and 200.

Another aspect of the present disclosure relates to a process for the hydroalkylation of benzene, wherein benzene and hydrogen with mole ratio ranging from about 0.2 to about 10 are passed through a composite hydroalkylation catalyst comprising molecular sieve, hydrogenation metal supported on inorganic metal oxide and binder. In an embodiment, the composite hydroalkylation catalyst is prepared in accordance with embodiments of the present disclosure and includes including the steps of: (a) effecting impregnation of a hydrogenation metal on an inorganic oxide to form a metal impregnated inorganic oxide; (b) effecting calcination of the metal impregnated inorganic oxide at a temperature ranging from 250° C. to 500° C. for a time period ranging from 1 hour to 15 hours to obtain a calcined metal impregnated inorganic oxide; (c) preparing a composite mixture comprising a molecular sieve, the calcined metal impregnated inorganic oxide and a binder; (d) kneading the composite mixture to obtain an extruded catalyst; and (e) effecting calcination of the extruded catalyst at a temperature ranging from 250° C. to 400° C. to obtain the composite hydroalkylation catalyst.

In an embodiment, the composite mixture comprises the molecular sieve, the calcined metal impregnated inorganic oxide and the binder in a weight ratio ranging from 1:1:1 to 50:30:1.

In an embodiment, the molecular sieve is selected from zeolite Y, zeolite X, zeolite Beta, Mordenite, MCM-22 and mixtures thereof. In an embodiment, the molecular sieve is zeolite Y. In an embodiment, the zeolite Y is USY zeolite. In an embodiment, the molecular sieve has $SiO_2/Al_2O_3$ ratio ranging between 4 and 200.

In an embodiment, the hydrogenation metal is selected from Palladium, Ruthenium, Nickel, Cobalt, Platinum, Rhodium, Rhenium, Tin, Zinc and mixtures thereof. In an embodiment, hydrogenation metal is nickel.

In an embodiment, the inorganic oxide comprises alumina, silica, silica-alumina, titania, zirconia and mixtures thereof. In an embodiment, the inorganic oxide comprises alumina.

In an embodiment, the binder is selected from clays, silica, alumina, silica-alumina, metal oxides and mixtures thereof. In an embodiment, the binder is alumina.

In an embodiment, the amount of metal loaded on the inorganic oxide is about 5 wt % to about 50 wt %. In an embodiment, the amount of metal loaded on the composite hydroalkylation catalyst is about 0.1 wt. % to about 30 wt. %.

Benzene hydroalkylation reaction can be carried out in a fixed bed micro-reactor unit. Particularly suitable is the distributed feed reactor for the purpose of carrying out hydroalkylation of benzene. Catalyst of the present disclosure can be dried and reduced before usage thereof in the hydroalkylation reaction (i.e. before being packed in the catalyst bed). After reduction, the reactor is cooled to the desired temperature and then pressurized to the operating pressure.

In an embodiment, the feed comprising benzene and hydrogen are added at different positions along the length of the distributed feed reactor.

In an embodiment, operating pressure of reactor zones is maintained at a pressure of about 5-60 bar. In an embodiment, operating temperature of the reactor zones is maintained at about 100° C. to about 300° C.

In an embodiment, the hydroalkylation reaction is carried out in a down-flow mode wherein, benzene and hydrogen are passed concurrently downwards through the catalyst bed. In an embodiment, the catalyst bed comprises the catalyst prepared in accordance with embodiments of the present disclosure.

In an embodiment, molar ratio of hydrogen to benzene introduced into any of the plurality of reactor zones ranges from 0.5:1 to 5:1. In an embodiment, the number of side feed entries into the reactor are at least 2.

In an embodiment, composition of the product exiting from any of the reactor zone of the distributed feed reactor is ~45-50 wt. % benzene, 1-5 wt. % cyclohexane, 30-40 wt. % cyclohexylbenzene, and 5-24 wt. % dicyclohexylbenzene.

It could be observed that, reaction temperature is an important factor affecting the selectivity for CHB. Lower temperature generally favours the selectivity for CHB. However, hydroalkylation of benzene is exothermic process, and limiting the temperature raise during the reaction is the key for higher CHB selectivity. Temperature raise can be controlled by reducing the saturation of benzene to cyclohexane, since this reaction is highly exothermic.

In the process of the present disclosure, better temperature control and lower saturation of benzene can be achieved by using a distributed feed reactor, wherein benzene and hydrogen are uniformly added to the reactor at different locations along the length of the reactor (as illustrated in FIG. 1). The molar ratio of benzene and hydrogen at the inlet of each reactor zone is maintained between 0.1:1 to about 5:1. The operating pressure of all reactor zones can be about 3-70 bar and the operating temperature of all the reactor zones can be about 100 to 300° C. Preferably, the reaction is carried out in liquid phase for better selectivity for CHB.

The reactor effluent stream can be fed to a gas liquid separator to recover the unconverted hydrogen, and this hydrogen can be recycled to the reactor. The separated effluents can then be feed to a multi-fractionator for separating reactor effluent stream into benzene and cyclohexane, CHB and DCHB streams.

The product composition (before fractionation into plurality of product streams) is 45-50 wt. % benzene, 1-5 wt. % cyclohexane, 30-40 wt. % cyclohexylbenzene (CHB) and 5-24 wt. % dicyclohexylbenzene (DCHB) in accordance with an embodiment.

Usage of the distributed feed reactor affords several fold technical advantages, illustratively: (a) by distributing benzene uniformly along the length of the reactor, higher concentration of benzene can be maintained along the reactor length thus leading to the formation of more CHB, and less DCHB and other impurities; (ii) higher benzene conversion can be achieved and hence, the reactor can be operated at higher throughputs leading to higher yield for CHB; and (iii) reaction temperature can be better controlled leading to avoidance of undesirable side reactions.

Typically hydroalkylation reaction is selective for the CHB, however, bi-products like cyclohexane, methylcyclopentane, methylcyclopentylbenzene, dicyclohexylbenzene, methyl cyclopentylcyclohexylbenzene are also formed, and hence, the benzene conversion levels are maintained at around 50% to avoid the formation of these bi-products. This necessitates the need for separating the benzene from the reaction products and recycle it back to the reactor for making the process more efficient. However, close boiling nature of benzene and cyclohexane makes it difficult to separate benzene from cyclohexane.

Accordingly, another aspect of the present disclosure relates to a process for operating a hydroalkylation reactor integrated with a catalytic reforming unit of an oil refinery. In an embodiment, the process includes the steps of: (i) subjecting a reactor effluent stream comprising unconverted hydrogen, benzene, cyclohexane, cyclohexylbenzene (CHB) and dicyclohexylbenzene (DCHB) from the hydroalkylation reactor to a separator to obtain unconverted hydrogen and a separated stream comprising the remainder of the components; (ii) subjecting the separated stream to fractional distillation to obtain a $C_6$ rich stream comprising cyclohexane and unconverted benzene and one or more streams comprising cyclohexylbenzene and dicyclohexylbenzene; (iii) blending the $C_6$ rich stream with naphtha feed to obtain a feed stream; (iv) feeding the feed stream to the catalytic reforming unit affording conversion of cyclohexane present in the feed stream to benzene; and (v) feeding benzene and hydrogen obtained from the catalytic reforming unit to the hydroalkylation reactor.

In an embodiment, the catalytic reforming unit comprises a Continuous Catalytic Reforming (CCR) unit. In an embodiment, the separator is a gas liquid separator. In an embodiment, the fractional distillation is done in a multi-component fractional distillation column. In an embodiment, the hydroalkylation reactor comprises a catalyst bed comprising the advantageous composite hydroalkylation catalyst realized in accordance with embodiments of the present disclosure.

In an embodiment, the $C_6$ rich stream comprising cyclohexane and unconverted benzene is recovered as top product from the distillation column. In an embodiment, cyclohexylbenzene rich stream is recovered as middle product from the distillation column. In an embodiment, dicyclohexylbenzene rich stream (DCHB) is recovered as bottom product from the distillation column. In an embodiment, the $C_6$ rich stream is blended with naphtha feed and it is fed to the catalytic reforming unit. In an embodiment, the amount of benzene in the feed in not more than 5 wt. %. In the CCR unit, cyclohexane present in the feed is converted into benzene without affecting benzene already present in the feed. Thus, the produced benzene can be used as a feed for the hydroalkylation reactor, eliminating the need for separating close boiling benzene and cyclohexane. Integrating the hydroalkylation process with CCR unit affords several fold technical advantages, illustratively: such integration not only makes the process more efficient in terms of availability of reactants, but also precludes the need for expensive process(es) for separating close boiling benzene and cyclohexane.

Figure 2:
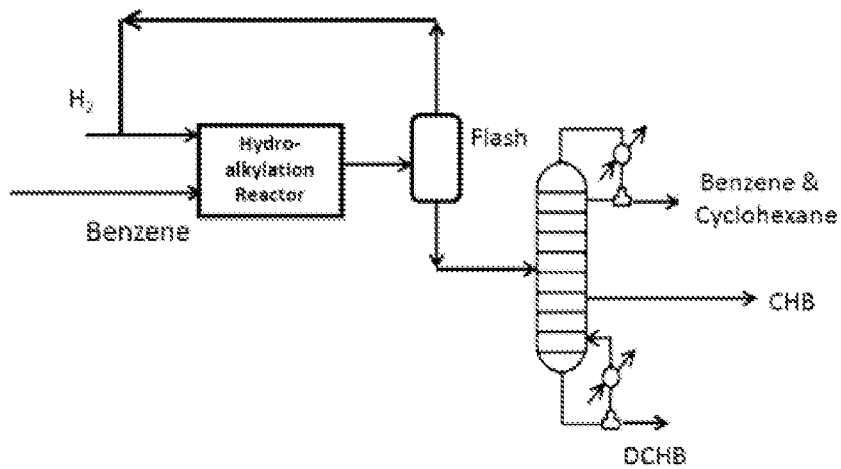
FIG. 2 illustrates an exemplary schematic diagram showing separation of the hydroalkylation products into individual fractions using distillation columns.
Figure 3:
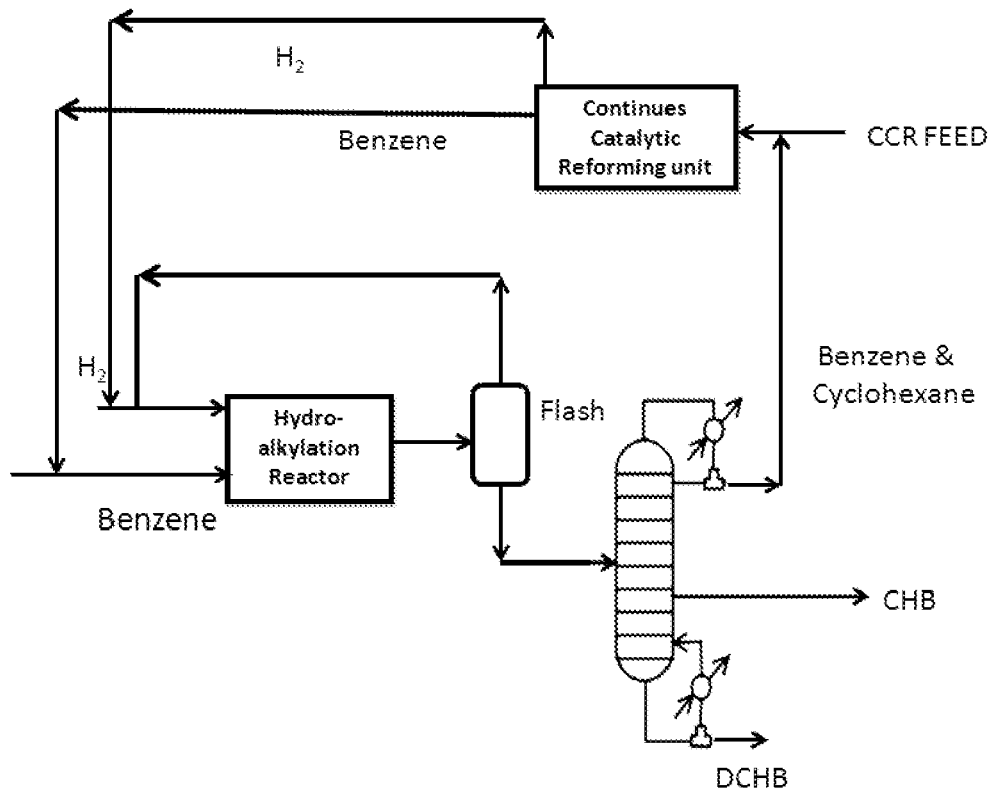
FIG. 3 illustrates an exemplary schematic diagram showing integration of the hydroalkylation reactor with the continuous catalytic reformer (CCR) unit of an oil refinery.

As can be seen from FIG. 2, the effluents from the reactor can be sent to a distillation column after separating unconverted hydrogen, wherein cyclohexane and unconverted benzene is recovered as top product ($C_6$ rich stream), cyclohexylbenzene rich stream is recovered as middle product and dicyclohexylbenzene rich stream (DCHB) is recovered as bottom product. $C_6$ rich stream can be blended with the naphtha feed of the CCR unit as can be seen from FIG. 3. In the CCR unit, cyclohexane present in the feed is converted into benzene without affecting the benzene already existing in the feed and thus, the produced benzene can be used as feed for hydroalkylation reactor, eliminating the need for separating benzene and cyclohexane.

EXAMPLES

Example 1

Method for the Preparation of Ni Supported γ-$Al_2O_3$

Ni supported on γ-$Al_2O_3$ is prepared by wet impregnation method using Nickel nitrate hexahydrate salt. A solution containing specified amount of nickel nitrate hexahydrate in 20 ml deionised water was prepared. To this solution, specified amount of gamma alumina was added slowly and continuously stirred for 4 hrs. After the impregnation, excess water was removed by drying the sample overnight at 120° C. The dried powder was calcined at 400° C. for 8 h in the presence of air. The amount of nickel nitrate hexahydrate used to produce 5 wt. %, 10 wt. %, 20 wt. % and 30 wt. % of Ni on 10 gm of γ-$Al_2O_3$ was 2.48 g, 4.95 g, 9.90 g and 14.87 g, respectively.

Example 2

Method for the Preparation of Composite Catalyst Containing 5 wt. % Ni/γ-$Al_2O_3$/USY12

A dry mixture was prepared by adding specified amount of 5 wt. % Ni/γ-$Al_2O_3$ powder. USY12 zeolite and binder. Prior to mixing. USY12 zeolite was dried at 120° C. overnight and the ammonium form of USY-12 was calcined at 550° C. for 10 hours to convert to the proton form. This mixture was continuously mixed till homogeneity. After homogeneous mixing, dough was prepared by kneading the mixture using 5% acetic acid solution. The kneaded sample was then extruded in the form of extrudates having a length of ~3 mm and diameter of about 1.5 mm. The extrudates were then dried at 120° C. overnight, followed by calcination in oxygen at 400° C. for 4 hrs. The ratio of Ni/γ-$Al_2O_3$ to USY12 zeolite to binder employed for catalyst preparation was 1.67:4:1. Final metal content of the catalyst was found to be around 1.25 wt. % and this catalyst sample was coded as CAT-1.

Example 3

Method for the Preparation of Composite Catalyst Containing 10 wt. % Ni/γ-Al$_2$O$_3$/USY12

A dry mixture was prepared by adding specified amount of 10 wt. % Ni/γ-Al$_2$O$_3$ powder, USY12 zeolite and binder. Prior to mixing, USY12 zeolite was dried at 120° C. overnight and the ammonium form of USY-12 was calcined at 550° C. for 10 hours to convert to H form. This mixture was continuously mixed till homogeneity. After homogeneous mixing, dough was prepared by kneading themixture using 5% acetic acid solution. The kneaded sample was then extruded in the form of extrudates having a length of ~3 mm and diameter of 1.5 mm, respectively. The extrudates were then dried at 120° C. overnight followed by calcination in oxygen at 400° C. for 4 hrs. The ratio of Ni/γ-Al$_2$O$_3$ to USY12 zeolite to binder employed for catalyst preparation was 1.67:4:1. Final metal content of the catalyst was around 2.5 wt. % and this catalyst sample was coded as CAT-2.

Example 4

Method for the Preparation of Composite Catalyst Containing 20 wt. % Ni/γ-Al$_2$O$_3$/USY12

A dry mixture was prepared by adding specified amount of 20 wt. % Ni/γ-Al$_2$O$_3$ powder, USY12 zeolite and binder. Prior to mixing, USY12 zeolite was dried at 120° C. overnight and the ammonium form of USY-12 was calcined at 550° C. for 10 hours to convert to H form. This mixture was continuously mixed till homogeneity. After homogeneous mixing, dough was prepared by kneading the mixture using 5% acetic acid solution. The kneaded sample was then extruded in the form of extrudates having a length of ~3 mm and diameter of 1.5 mm. The extrudates were then dried at 120° C. overnight followed by calcination in oxygen at 400° C. for 4 hrs. The ratio of Ni/γ-Al$_2$O$_3$ to USY12 zeolite to binder employed for catalyst preparation was 1.67:4:1. Final metal content of the catalyst was around 5 wt. % and this catalyst sample was coded as CAT-3.

Example 5

Method for the Preparation of Composite Catalyst Containing 30 wt. % Ni/γ-Al$_2$O$_3$/USY12

A dry mixture was prepared by adding specified amount of 30 wt. % Ni/γ-Al$_2$O$_3$ powder, USY12 zeolite and binder. Prior to mixing, USY-12 zeolite was dried at 120° C. overnight and the ammonium form of USY-12 was calcined at 550° C. for 10 hours to convert to H form. This mixture was continuously mixed till homogeneity. After homogeneous mixing, dough was prepared by kneading the mixture using 5% acetic acid solution. The kneaded sample was then extruded in the form of extrudates having a length of ~3 mm and diameter of 1.5 mm, respectively. The extrudates were then dried at 120° C. overnight followed by calcination in oxygen at 400° C. for 4 hrs. The ratio of Ni/γ-Al$_2$O$_3$ to USY12 zeolite to binder employed for catalyst preparation was 1.67:4:1. Final metal content of the catalyst was around 7.5 wt. % and this catalyst sample was coded as CAT-4.

Example 6

Method for the Preparation of Composite Catalyst Containing 20 wt. % Ni/γ-Al$_2$O$_3$/USY12 with 35 wt. % zeolites A dry mixture was prepared by adding specified amount of 20 wt. % Ni/γ-Al$_2$O$_3$ powder, USY12 zeolite and binder. Prior to mixing USY12 zeolite was dried at 120° C. overnight and the ammonium form of USY-12 was calcined at 550° C. for 10 hours to convert to H form. This mixture was continuously mixed till homogeneity. After homogeneous mixing, dough was prepared by kneading the mixture using 5% acetic acid solution. The kneaded sample was then extruded in the form of extrudates having a length of ~3 mm and diameter of 1.5 mm, respectively. The extrudates were then dried at 120° C. overnight followed by calcination in oxygen at 400° C. for 4 h. The weight % of USY12 zeolite in the composite catalyst was 35%. Final metal content of the catalyst was around 5 wt. %. This catalyst sample was coded as CAT-5.

Example 7

Method for the Preparation of Composite Catalyst Containing 20 wt. % Ni/γ-Al$_2$O$_3$/USY12 with 45 wt. % Zeolites A dry mixture was prepared by adding specified amount of 20 wt. % Ni/γ-Al$_2$O$_3$ powder. USY-12 zeolite and binder. Prior to mixing USY12 zeolite was dried at 120° C. overnight and the ammonium form of USY-12 was calcined at 550° C. for 10 hours to convert to 14 form. This mixture was continuously mixed till homogeneity. After homogeneous mixing, dough was prepared by kneading the mixture using 5% acetic acid solution. The kneaded sample was then extruded in the form of extrudates having a length of ~3 mm and diameter of 1.5 mm, respectively. The extrudates were then dried at 120° C. overnight followed by calcination in oxygen at 400° C. for 4 h. The weight % of USY12 zeolite in the composite catalyst was 45%. Final metal content of the catalyst was around 5 wt. %. This catalyst sample was coded as CAT-6.

Example 8

Method for the Preparation of Composite Catalyst Containing 20 wt. % Ni/γ-Al$_2$O$_3$/USY12 with 55 wt. % of Zeolites A dry mixture was prepared by adding known amount of 20 wt. % Ni/γ-Al$_2$O$_3$ powder, USY12 zeolite and binder. Prior to mixing USY12 zeolite was dried at 120° C. overnight and the ammonium form of USY-12 was calcined at 550° C. for 10 hours to convert to H form. This mixture was continuously mixed till homogeneity. After homogeneous mixing, dough was prepared by kneading the mixture using 5% acetic acid solution. The kneaded sample was then extruded in the form of extrudates having a length of ~3 mm and diameter of 1.5 mm, respectively. The extrudates were then dried at 120° C. overnight followed by calcination in oxygen at 400° C. for 4 h. The weight % of USY12 zeolite in the composite catalyst was 55%. Final metal content of the catalyst was around 5 wt. %. This catalyst sample was codes as CAT-7.

Example 9

Method for the Preparation of Composite Catalyst Containing 20 wt. % Ni/γ-Al$_2$O$_3$/USY12 with 75 wt. % of Zeolites A dry mixture was prepared by adding known amount of 20 wt. % Ni/γ-Al$_2$O$_3$ powder, USY12 zeolite and binder. Prior to mixing USY12 zeolite was dried at 120° C. overnight and the ammonium form of USY-12 was calcined at 550° C. for 10 hours to convert to H form. This mixture was continuously mixed till homogeneity, After homogeneous mixing, dough was prepared by kneading the mixture using 5% acetic acid solution. The kneaded sample was then extruded inthe form of extrudates having a length of ~3 mm and diameter of 1.5 mm, respectively. The extrudates were then dried at 120° C. overnight followed by calcination in oxygen at 400° C. for 4 h. The weight % of USY12 zeolite in the composite catalyst was 75%. Final metal content of the catalyst was around 5 wt. %. This catalyst sample was codes as CAT-8.

Example 10

Comparative Example—Catalyst Containing 20 wt. % Ni/γ-Al$_2$O$_3$/USY12

Composite catalyst containing 20 wt. % Ni/γ-Al$_2$O$_3$/USY12 was prepared as mentioned in example 4. However in this example, uncalcined 20 wt. % Ni/γ-Al$_2$O$_3$ was used in the composite catalyst preparation and catalyst sample was coded as CAT-3C.

Measurement of Activity and Selectivity of the Catalysts

All the catalyst recipes were tested for hydroalkylation of benzene in a fixed bed reactor. 5 g of calcined catalyst extrudate diluted with inert material (SiC) was packed in a stainless steel fixed bed reactor. The catalyst was then dried overnight at 130° C. under nitrogen flow and reduced at specific temperature under a constant H$_2$ flow of 100 ml/min at atmospheric pressure for 5 h. After reduction of the metal, the catalyst was used for hydroalkylation reaction. The reaction was carried out at a temperature range of 150° C., WHSV of 0.8-1.2 h-1, with H$_2$/Benzene mole ratio of 1 at 20 bar pressure. The product composition analysis was done using GC-FID to obtain catalyst selectivity at a desired conversion level. The activity and selectivity data for different catalysts are tabulated in the Table 1.

TABLE 1

Comparison of activity and selectivity of different catalysts for CHB selectivity at similar benzene conversion

| Sample | Reaction conditions | Benzene Conversion (%) | CHB Selectivity (%) | Yield of CHB (%) |
|---|---|---|---|---|
| CAT-1 | T = 150° C., P = 20 bar, WHSV = 1 hr$^{-1}$ | 4 | 85 | 3.4 |
| CAT-2 | T = 150° C, P = 20 bar, WHSV = 1 hr$^{-1}$ | 9 | 94 | 8.5 |
| CAT-3 | T = 150° C., P = 20 bar, WHSV = 1.5 hr$^{-1}$ | 45 | 74 | 33.3 |
| CAT-4 | T = 150° C, P = 20 bar, WHSV = 1.5 hr$^{-1}$ | 45 | 75 | 33.7 |
| CAT-5 | T = 150° C., P = 20 bar, WHSV = 1 hr$^{-1}$ | 42 | 69 | 29 |
| CAT-6 | T = 150° C, P = 20 bar, WHSV = 1 hr$^{-1}$ | 40 | 68 | 27.2 |
| CAT-7 | T = 150° C., P = 20 bar, WHSV = 1.5 hr$^{-1}$ | 41 | 68 | 27.9 |
| CAT-8 | T = 150° C, P = 20 bar, WHSV = 2.5 hr$^{-1}$ | 44 | 78 | 34.3 |
| CAT-3C | T = 150° C., P = 20 bar, WHSV = 1.5 hr$^{-1}$ | 6 | 93 | 5.6 |

CAT-3 and CAT-4 having Ni loading of 5 and 7.5 wt. % showed superior activity for hydroalkylation of benzene whereas catalyst with lower metal loading (CAT-1 and CAT-2) showed very low hydroalkylation activity. Increasing zeolite content of the catalyst favoured hydroalkylation activity and CHB selectivity of the catalyst. Among all the catalysts with different zeolite contents (CAT-3, CAT-5, CAT-6, CAT-7, CAT-8), CAT-3 and CAT-8 exhibited superior activity and CHB selectivity. Further, comparative example (CAT-3C) established that the composite hydroalkylation catalyst prepared using a process that includes two (2) calcination steps viz. (i) effecting calcination of the metal impregnated inorganic oxide; and (ii) effecting calcination of the extruded catalyst affords dramatic improvement in conversion of mononuclear aromatic hydrocarbon (Benzene) and the yield of the hydroalkyled mononuclear aromatic hydrocarbon (e.g. CHB). Particularly, the composite catalyst afforded ~6 fold increase in the yield of the CHB.

Example 11

Effect of Catalyst Reduction Temperature on Activity and Selectivity of the Catalysts CAT-3 recipes were tested for hydroalkylation of benzene in a fixed bed reactor. 5 g of calcined catalyst extrudate diluted with inert material (SiC) was packed in a stainless steel fixed bed reactor. The catalyst was then dried overnight at 130° C. under nitrogen flow and reduced at 250° C. temperature under a constant H$_2$ flow of 100 ml/min at atmospheric pressure for 5 h. After reduction of the metal, the catalyst was used for hydroalkylation reaction. The reaction was carried out at a temperature range of 150° C., WHSV of 1-3 h$^{-1}$, with H$_2$/Benzene mole ratio of 1 at 20 bar pressure. This catalyst sample was codes as CAT-3 (250).

Example 12

Effect of Catalyst Reduction Temperature on Activity and Selectivity of the Catalysts CAT-3 recipes were tested for hydroalkylation of benzene in a fixed bed reactor. Typically, 5 g of calcined catalyst extrudate diluted with inert material (SiC) was packed in a stainless steel fixed bed reactor. The catalyst was then dried overnight at 130° C. under nitrogen flow and reduced at 300° C. temperature under a constant H$_2$ flow of 100 ml/min at atmospheric pressure for 5 h, After reduction of the metal, the catalyst was used for hydroalkylation reaction. The reaction was carried out at a temperature range of 150° C., WHSV of 0.8-1.2 h-1, with H$_2$/Benzene mole ratio of 1 at 20 bar pressure. This catalyst sample was codes as CAT-3 (300).

Example 13

Effect of Catalyst Reduction Temperature on Activity and Selectivity of the Catalysts CAT-3 recipes were tested for hydroalkylation of benzene in a fixed bed reactor. 5 g of calcined catalyst extrudate diluted with inert material (SiC) was packed in a stainless steel fixed bed reactor. The catalyst was then dried overnight at 130° C. under nitrogen flow and reduced at 350° C. temperature under a constant H$_2$ flow of 100 ml/min at atmospheric pressure for 5 h. After reduction of the metal, the catalyst was used for hydroalkylation reaction. The reaction was carried out at a temperature range of 150° C., WHSV of 0.8-1.2 h-1, with H$_2$/Benzene mole ratio of 1 at 20 bar pressure. This catalyst sample was codes as CAT-3 (350). The activity and selectivity data for different catalysts are tabulated in the Table 2.

TABLE 2

Comparison of activity and selectivity of different catalysts for CHB selectivity at similar benzene conversion

| Sample | Reaction conditions | Benzene Conversion (%) | CHB Selectivity (%) | Yield of CHB (%) |
| --- | --- | --- | --- | --- |
| CAT-3 (250) | T = 150° C., P = 20 bar, WHSV = 1.2 hr$^{-1}$ | 10 | 70 | 7.0 |
| CAT-3 (300) | T = 150° C., P = 20 bar, WHSV = 1.5 hr$^{-1}$ | 45 | 74 | 33.3 |
| CAT-3 (350) | T = 150° C., P = 20 bar, WHSV = 2 hr$^{-1}$ | 64 | 47 | 30.1 |
| CAT-3 (350) | T = 150° C., P = 20 bar, WHSV = 3 hr$^{-1}$ | 42 | 56 | 23.5 |

CAT-3 was reduced at different temperatures to study the effect of catalyst reduction temperature on the hydroalkylation activity and selectivity of the catalyst. Catalyst reduced at lower temperature (250° C.) showed lower activity for the hydroalkylation reaction whereas catalyst reduced at higher temperature (350° C.) showed higher activity but the selectivity for CHB was inferior. Catalyst reduced at intermediate temperature (300° C.) showed superior selectivity for CHB at reasonable benzene conversion.

Example 14

Effect of Catalyst Reduction Time on Activity of the Catalyst

CAT-3 recipes were tested for hydroalkylation of benzene in a fixed bed reactor. Typically, 5 g of calcined catalyst extrudate diluted with inert material (SiC) was packed in a stainless steel fixed bed reactor. The catalyst was then dried overnight at 130° C. under nitrogen flow and reduced at 300° C. temperature under a constant H$_2$ flow of 100 mi/min at atmospheric pressure for 8 h. After reduction of the metal, the catalyst was used for hydroalkylation reaction. The reaction was carried out at a temperature range of 150° C., WHSV of 0.8-1.2 h-1, with H$_2$/Benzene mole ratio of 1 at 20 bar pressure. This catalyst sample was codes as CAT-3 (300-8 hr).

Example 15

Effect of Catalyst Reduction Time on Activity of the Catalyst

CAT-3 recipes were tested for hydroalkylation of benzene in a fixed bed reactor. Typically, 5 g of calcined catalyst extrudate diluted with inert material (SiC) was packed in a stainless steel fixed bed reactor. The catalyst was then dried overnight at 130° C. under nitrogen. flow and reduced at 300° C. temperature under a constant H$_2$ flow of 100 ml/min at atmospheric pressure for 12 h. After reduction of the metal, the catalyst was used for hydroalkylation reaction. The reaction was carried out at a temperature range of 150° C., WHSV of 0.8-1.2 h-1, with H$_2$/ Benzene mole ratio of 1 at 20 bar pressure. This catalyst sample was codes as CAT-3 (300-12 hr).

Example 16

Effect of Catalyst Reduction Time on Activity of the Catalyst

CAT-3 recipes were tested for hydroalkylation of benzene in a fixed bed reactor. Typically. 5 g of calcined catalyst extrudate diluted with inert material (SiC) was packed in a stainless steel fixed bed reactor. The catalyst was then dried overnight at 130° C. under nitrogen flow and reduced at 300° C. temperature under a constant H$_2$ flow of 100 ml/min at atmospheric pressure for 17 h. After reduction of the metal, the catalyst was used for hydroalkylation reaction. The reaction was carried out at a temperature range of 150° C., WHSV of 0.8-1.2 h-1, with H$_2$/Benzene mole ratio of 1 at 20 bar pressure. This catalyst sample was codes as CAT-3 (300-17 hr).

TABLE 3

Comparison of activity and selectivity of different catalysts
for CHB selectivity at similar benzene conversion

| Sample | Reaction conditions | Benzene Conversion (%) | CHB Selectivity (%) | Yield of CHB (%) |
|---|---|---|---|---|
| CAT-3 (300-5 h) example 10 | T = 150° C., P = 20 bar, WHSV = 1.5 hr$^{-1}$ | 45 | 74 | 33.3 |
| CAT-3 (300-8 h) | T = 150° C., P = 20 bar, WHSV = 2.5 hr$^{-1}$ | 43 | 73 | 31.4 |
| CAT-3 (300-12 h) | T = 150° C., P = 20 bar, WHSV = 2.5 hr$^{-1}$ | 44 | 72 | 31.7 |
| CAT-3 (300-17 h) | T = 150° C., P = 20 bar, WHSV = 3 hr$^{-1}$ | 43 | 70 | 30.1 |

CAT-3 was reduced at 300° C. for different time durations to study the effect of catalyst reduction time on the hydroalkylation activity and selectivity of the catalyst. Catalyst reduced for 8 hrs showed benzene conversion of 43% at space velocity of 2.5 hr$^{-1}$. Whereas catalyst reduced for 12 hrs and 17 hrs showed similar conversion at space velocity of 2.5 and 3 hr$^{-1}$ respectively. Furthermore, catalyst reduced for 5 hrs showed benzene conversion of 45% at space velocity of 1.5 hr$^{-1}$. Accordingly, catalyst reduction time of 8-12 hrs is found to optimal w.r.t to activity and CHB selectivity of the catalyst.

Advantages

The present disclosure provides an improved composite hydroalkylation catalyst.

The present disclosure provides an improved method for preparation of a composite hydroalkylation catalyst.

The present disclosure provides an efficient process for converting benzene to CHB using a distributed feed reactor.

The present disclosure provides an approach to integrate hydroalkylation process with Continuous Catalytic Reforming (CCR) unit of a refinery, improving the efficiency and economy of production of CHB from benzene.

We claim:

1. A process for preparing a composite hydroalkylation catalyst, said process comprising the steps of:
   (a) effecting impregnation of a hydrogenation metal on an inorganic oxide to form a metal impregnated inorganic oxide;
   (b) effecting calcination of the metal impregnated inorganic oxide at a temperature ranging from 250° C. to 500° C. for a time period ranging from 1 hour to 15 hours to obtain a calcined metal impregnated inorganic oxide;
   (c) preparing a composite mixture comprising a molecular sieve, the calcined metal impregnated inorganic oxide and a binder;
   (d) kneading the composite mixture to obtain an extruded catalyst; and
   (e) effecting calcination of the extruded catalyst at a temperature ranging from 250° C. to 400° C. to obtain the composite hydroalkylation catalyst.

2. The method as claimed in claim 1, wherein the composite hydroalkylation catalyst is subjected to reduction at a temperature ranging from 200° C. to 500° C. for a time period ranging from 3 hours to 20 hours.

3. The method as claimed in claim 1, wherein said composite mixture comprises the molecular sieve, the calcined metal impregnated inorganic oxide and the binder in a weight ratio ranging from 1:1:1 to 50:30:1.

4. The method as claimed in claim 1, wherein the step of calcination of the metal impregnated inorganic oxide is effected at a temperature ranging from 250° C. to 500° C. in air for a time period ranging from 3 hours to 10 hours.

5. The method as claimed in claim 1, wherein the step of calcination of the extruded catalyst is effected at a temperature ranging from about 250° C. to about 400° C. under constant air flow for a time period ranging from 1 hour to 5 hours.

6. The method as claimed in claim 1, wherein the molecular sieve is selected from zeolite Y, zeolite X, zeolite Beta, Mordenite, MCM-22 and mixtures thereof, and wherein the hydrogenation metal is selected from Palladium, Ruthenium, Nickel, Cobalt, Platinum, Rhodium, Rhenium, Tin and mixtures thereof, further wherein the inorganic oxide comprises alumina, silica, silica-alumina, titania, zirconia and mixtures thereof, further wherein the binder is selected from clays, silica, alumina, silica-alumina, metal oxides and mixtures thereof.

7. The method as claimed in claim 1, wherein the molecular sieve is zeolite Y, said zeolite Y being USY zeolite, the hydrogenation metal is nickel, inorganic oxide comprises alumina and binder is alumina.

8. The method as claimed in claim 1, wherein amount of the metal impregnated on the inorganic oxide ranges from 5 wt % to 50 wt %.

9. The method as claimed in claim 1, wherein amount of the metal impregnated in the composite hydroalkylation catalyst ranges from 0.1 wt. % to 30 wt. %.

10. A process for hydroalkylation of a mononuclear aromatic hydrocarbon in a distributed feed reactor having a plurality of reactor zones, said process comprising the steps of:

feeding a stream comprising the mononuclear aromatic hydrocarbon and hydrogen at one or more positions along length of the distributed feed reactor; and
   effecting passage of the mononuclear aromatic hydrocarbon and hydrogen concurrently through a catalyst bed to effect hydroalkylation of the mononuclear aromatic hydrocarbon, said catalyst bed comprising a composite hydroalkylation catalyst, wherein said composite hydroalkylation catalyst is prepared by a process comprising the steps of: (a) effecting impregnation of a hydrogenation metal on an inorganic oxide to form a metal impregnated inorganic oxide; (b) effecting calcination of the metal impregnated inorganic oxide at a temperature ranging from 250° C. to 500° C. for a time period ranging from 1 hour to 15 hours to obtain a calcined metal impregnated inorganic oxide; (c) preparing a composite mixture comprising a molecular sieve, the calcined metal impregnated inorganic oxide and a binder; (d) preparing an extruded catalyst from the composite mixture; and (e) effecting calcination of the extruded catalyst at a temperature ranging from 250° C. to 400° C. to obtain the composite hydroalkylation catalyst.

11. The process as claimed in claim 10, wherein the composite hydroalkylation catalyst is subjected to reduction at a temperature ranging from 200° C. to 500° C. for a time period ranging from 3 hours to 20 hours before being packed in the catalyst bed.

12. The process as claimed in claim 10, wherein the mononuclear aromatic hydrocarbon is benzene, and wherein the reactor zones are operated at a pressure ranging from 5-60 bar and at a temperature ranging from 100° C. to 300° C., further wherein molar ratio of hydrogen to benzene fed to the reactor ranges from 0.5:1 to 5:1.

13. The process as claimed in claim 10, wherein the molecular sieve is selected from zeolite Y, zeolite X, zeolite Beta, Mordenite, MCM-22 and mixtures thereof, and wherein the hydrogenation metal is selected from Palladium, Ruthenium, Nickel, Cobalt, Platinum, Rhodium, Rhenium, Tin, Zinc and mixtures thereof, further wherein the inorganic oxide comprises alumina, silica, silica-alumina, titanic, zirconia and mixtures thereof, further wherein the binder is selected from clays, silica, alumina, silica-alumina, metal oxides and mixtures thereof, further wherein amount of the metal impregnated in the composite hydroalkylation catalyst ranges from 0.1 wt. % to 30 wt. %.

14. The method as claimed in claim 10, wherein the molecular sieve is zeolite Y, said zeolite Y being USY zeolite, the hydrogenation metal is nickel, inorganic oxide comprises alumina and binder is alumina, further wherein amount of the metal impregnated in the composite hydroalkylation catalyst ranges from 0.1 wt. % to 30 wt. %.

\* \* \* \* \*